(12) United States Patent
Horton et al.

(10) Patent No.: US 12,011,195 B1
(45) Date of Patent: Jun. 18, 2024

(54) SURGICAL IMPLANT AND METHOD OF USING SAME

(71) Applicant: NuTech Spine, Inc., Birmingham, AL (US)

(72) Inventors: Kenneth L. Horton, Watersound, FL (US); Jeffery S. Roh, Seattle, WA (US)

(73) Assignee: NuTech Spine, Inc., Birmingham, AL (US)

( * ) Notice: Subject to any disclaimer, the term of this patent is extended or adjusted under 35 U.S.C. 154(b) by 123 days.

(21) Appl. No.: 16/783,414

(22) Filed: Feb. 6, 2020

Related U.S. Application Data

(63) Continuation of application No. 15/722,603, filed on Oct. 2, 2017, now Pat. No. 10,595,911, which is a continuation of application No. 29/610,431, filed on Jul. 12, 2017, now Pat. No. Des. 831,828.

(51) Int. Cl.
| | | |
|---|---|---|
| *A61F 2/46* | (2006.01) | |
| *A61B 17/70* | (2006.01) | |
| *A61F 2/30* | (2006.01) | |
| *A61F 2/44* | (2006.01) | |

(52) U.S. Cl.
CPC ........ *A61B 17/7064* (2013.01); *A61F 2/4455* (2013.01); *A61F 2/4611* (2013.01); *A61F 2002/30405* (2013.01); *A61F 2002/30471* (2013.01)

(58) Field of Classification Search
CPC .. A61B 17/7064; A61F 2/4455; A61F 2/4611; A61F 2002/30405; A61F 2002/30471
See application file for complete search history.

(56) References Cited

U.S. PATENT DOCUMENTS

| | | |
|---|---|---|
| D524,941 S | 7/2006 | Dixon et al. |
| D581,538 S | 11/2008 | Horton |
| D612,500 S | 3/2010 | Strobel et al. |
| D621,046 S | 8/2010 | Strobel et al. |
| D621,047 S | 8/2010 | Strobel et al. |
| D629,106 S | 12/2010 | Horton et al. |
| D629,519 S | 12/2010 | Horton |
| D629,904 S | 12/2010 | Horton |
| D629,905 S | 12/2010 | Horton et al. |
| 8,021,392 B2 | 9/2011 | Petersen |
| 8,231,661 B2 | 7/2012 | Carls et al. |
| D697,209 S | 1/2014 | Walthall, Jr. et al. |
| 9,271,742 B2 | 3/2016 | Asfora |
| 9,358,057 B1 | 6/2016 | Whipple et al. |
| 9,943,340 B2 | 4/2018 | Whipple et al. |

(Continued)

*Primary Examiner* — Nicholas J Plionis
(74) *Attorney, Agent, or Firm* — C. Brandon Browning; Ilya S. Mirov; Erin R. Gaddes

(57) ABSTRACT

A method of stabilizing a facet joint by providing a fixation member with a substantially stadium-shaped cross-section, forming a void having a substantially stadium-shaped cross-section within the facet joint and inserting the fixation member into the void. The void is formed by engaging a first drill guide with the facet joint having two drill guide paths and drilling two spaced-apart or slightly overlapping passageways within the face joint, followed by engaging a second drill guide with the facet joint and drilling a third passageway between the two other passageways. The fixation member includes a tapered, anti-migration section configured for engaging the opposing articular surfaces of the joint.

10 Claims, 13 Drawing Sheets

(56) References Cited

U.S. PATENT DOCUMENTS

| | | |
|---|---|---|
| 2003/0065330 A1 | 4/2003 | Zucherman et al. |
| 2005/0165399 A1* | 7/2005 | Michelson ............ A61F 2/4611 |
| | | 623/17.11 |
| 2006/0111782 A1 | 5/2006 | Petersen |
| 2008/0046084 A1 | 2/2008 | Sledge |
| 2011/0054613 A1 | 3/2011 | Hansen |
| 2011/0106259 A1* | 5/2011 | Lindenmann ......... A61F 2/4684 |
| | | 623/17.16 |
| 2011/0230965 A1* | 9/2011 | Schell ................ A61B 17/7064 |
| | | 606/86 A |
| 2012/0010659 A1* | 1/2012 | Angert ............... A61B 17/7064 |
| | | 606/247 |
| 2012/0259365 A1 | 10/2012 | Richelsoph |
| 2012/0330360 A1 | 12/2012 | Nishida |
| 2015/0088200 A1 | 3/2015 | Lins |

* cited by examiner

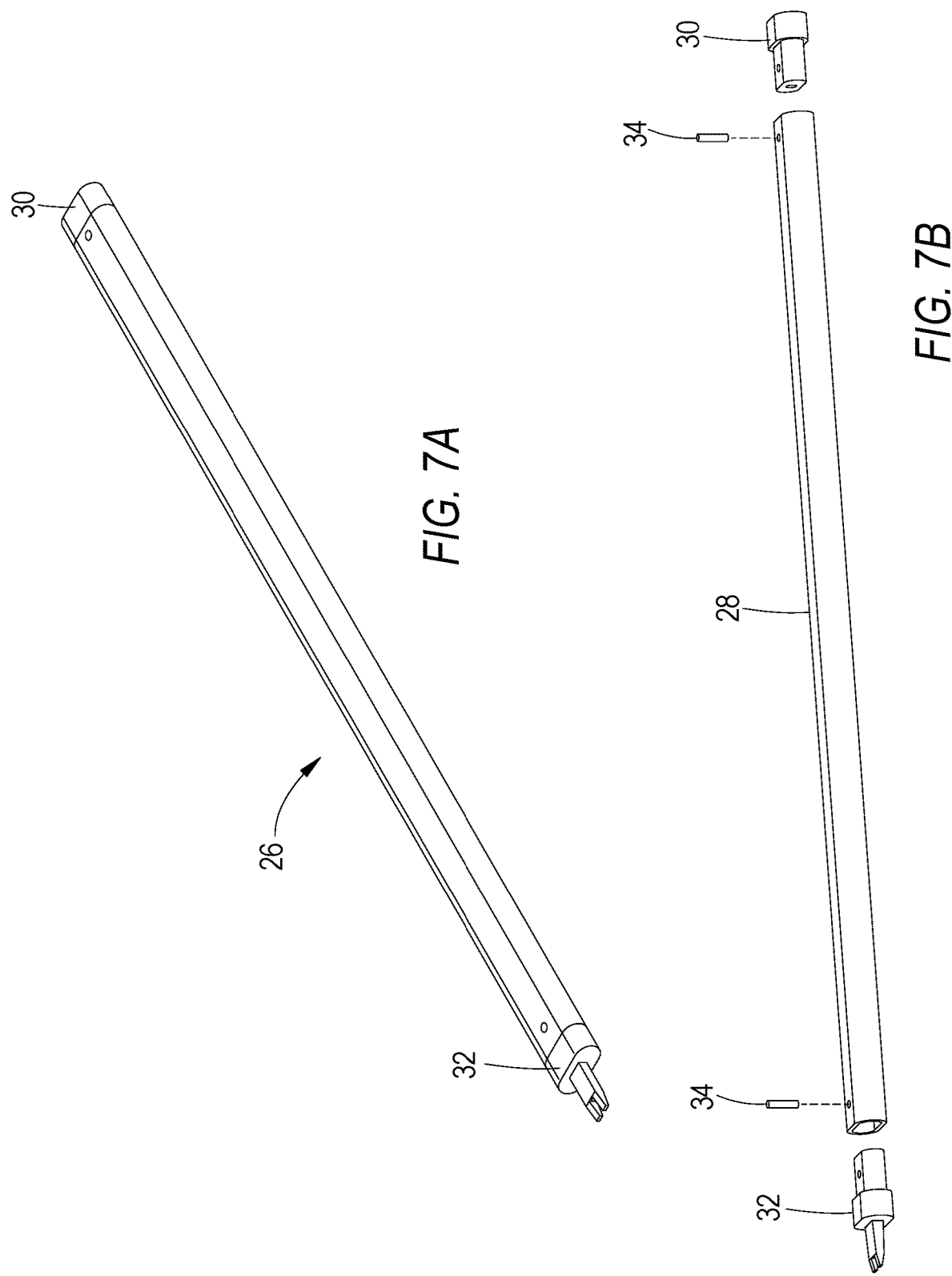

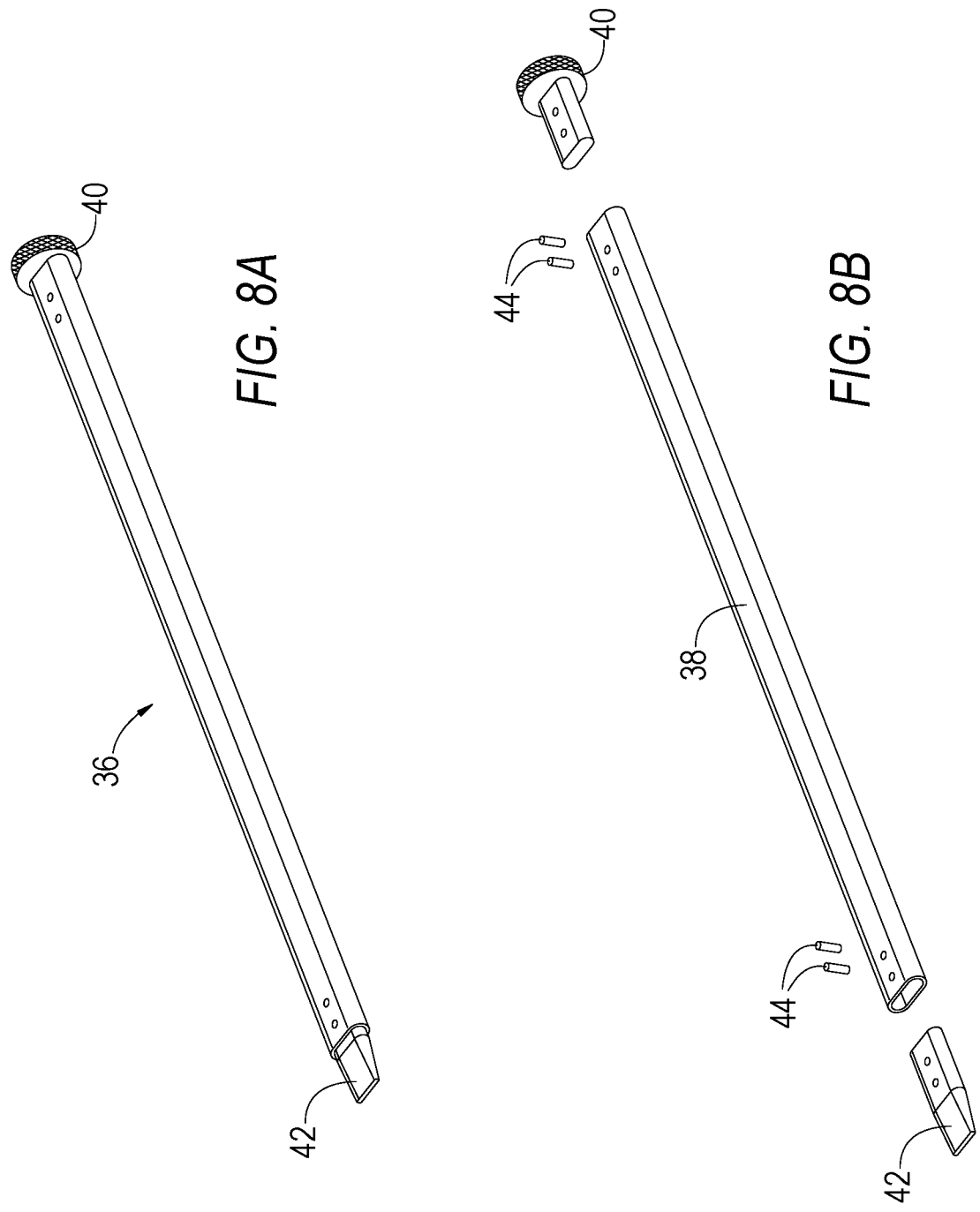

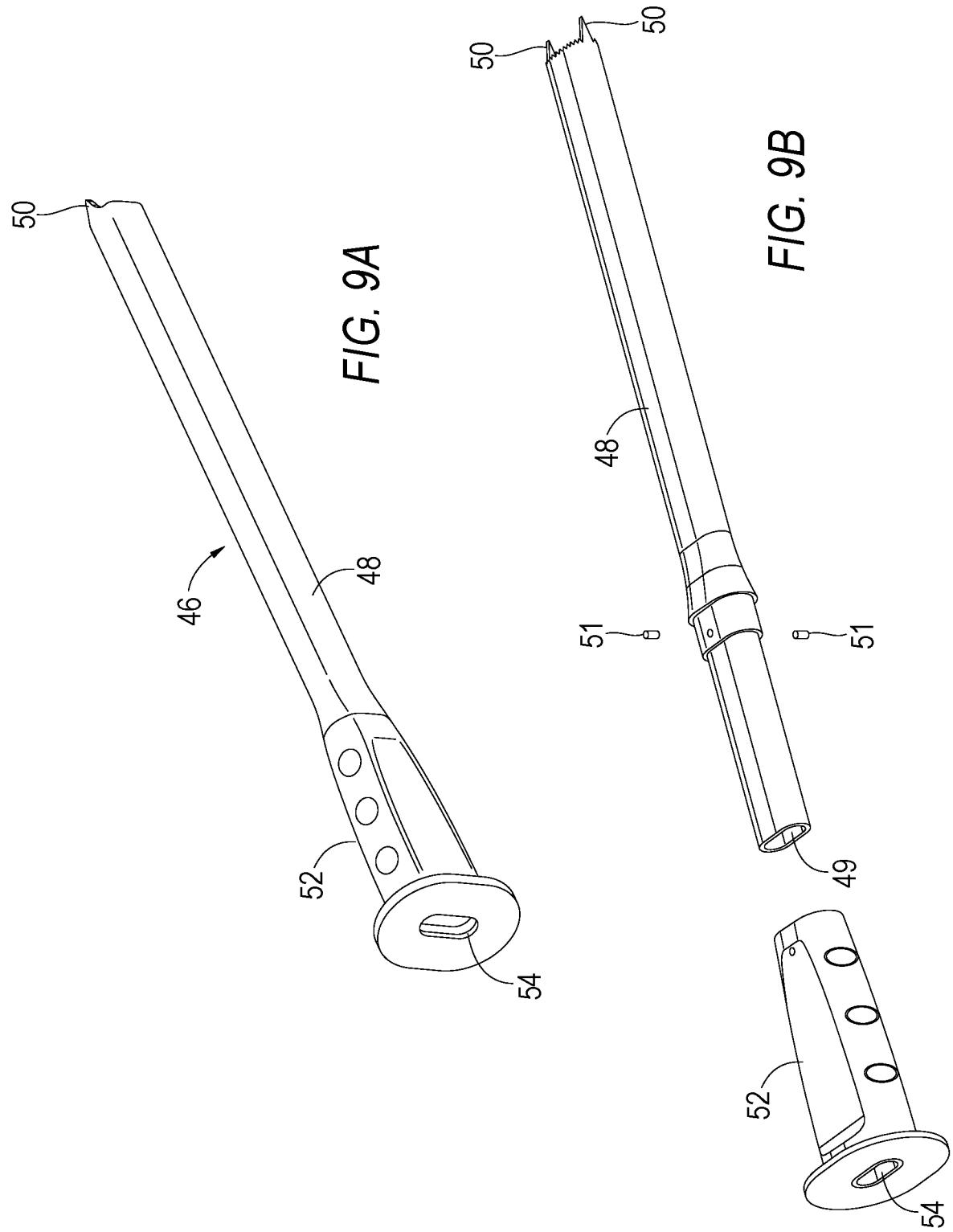

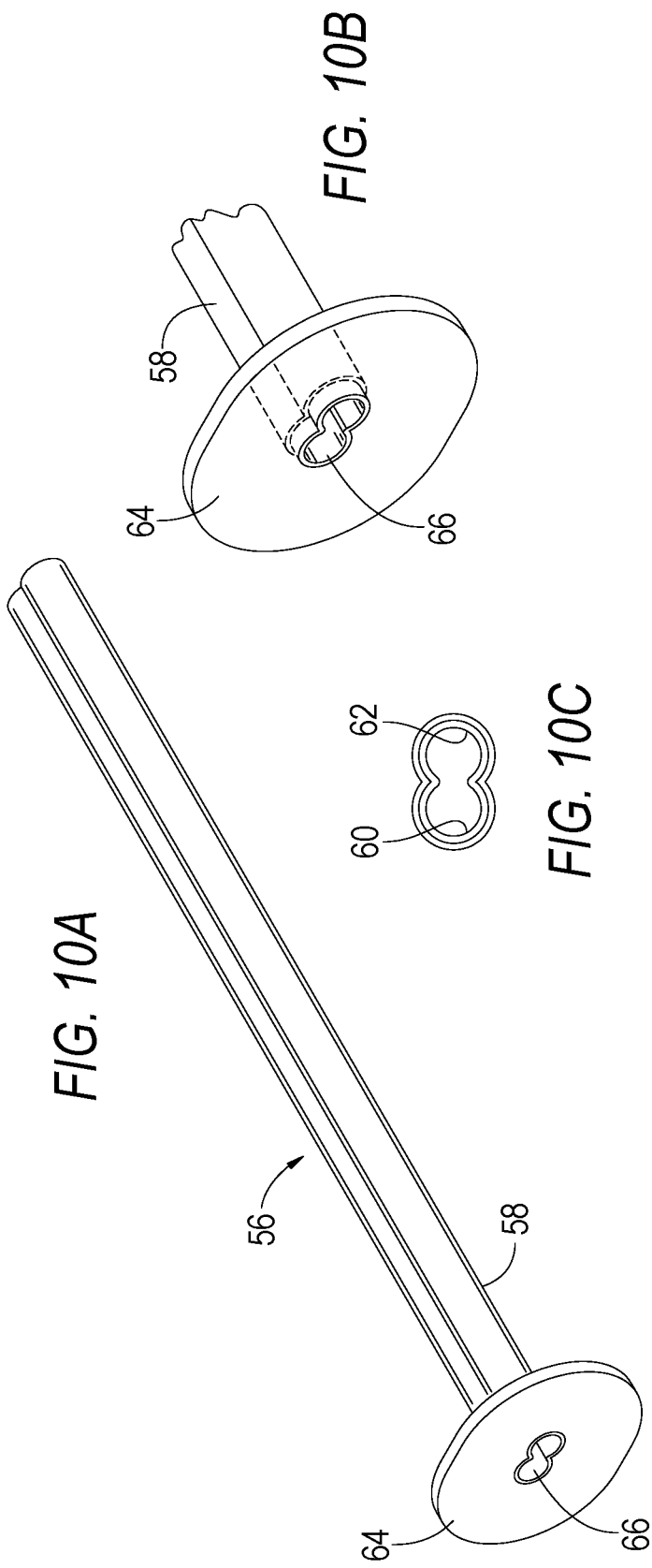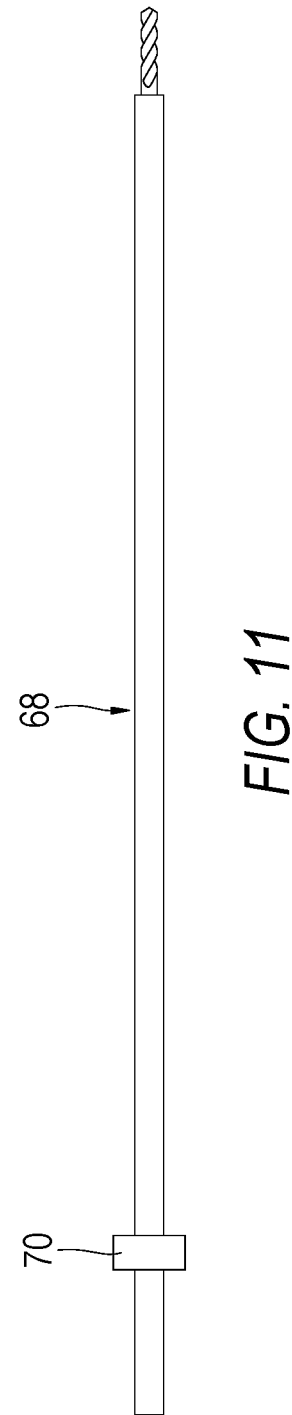

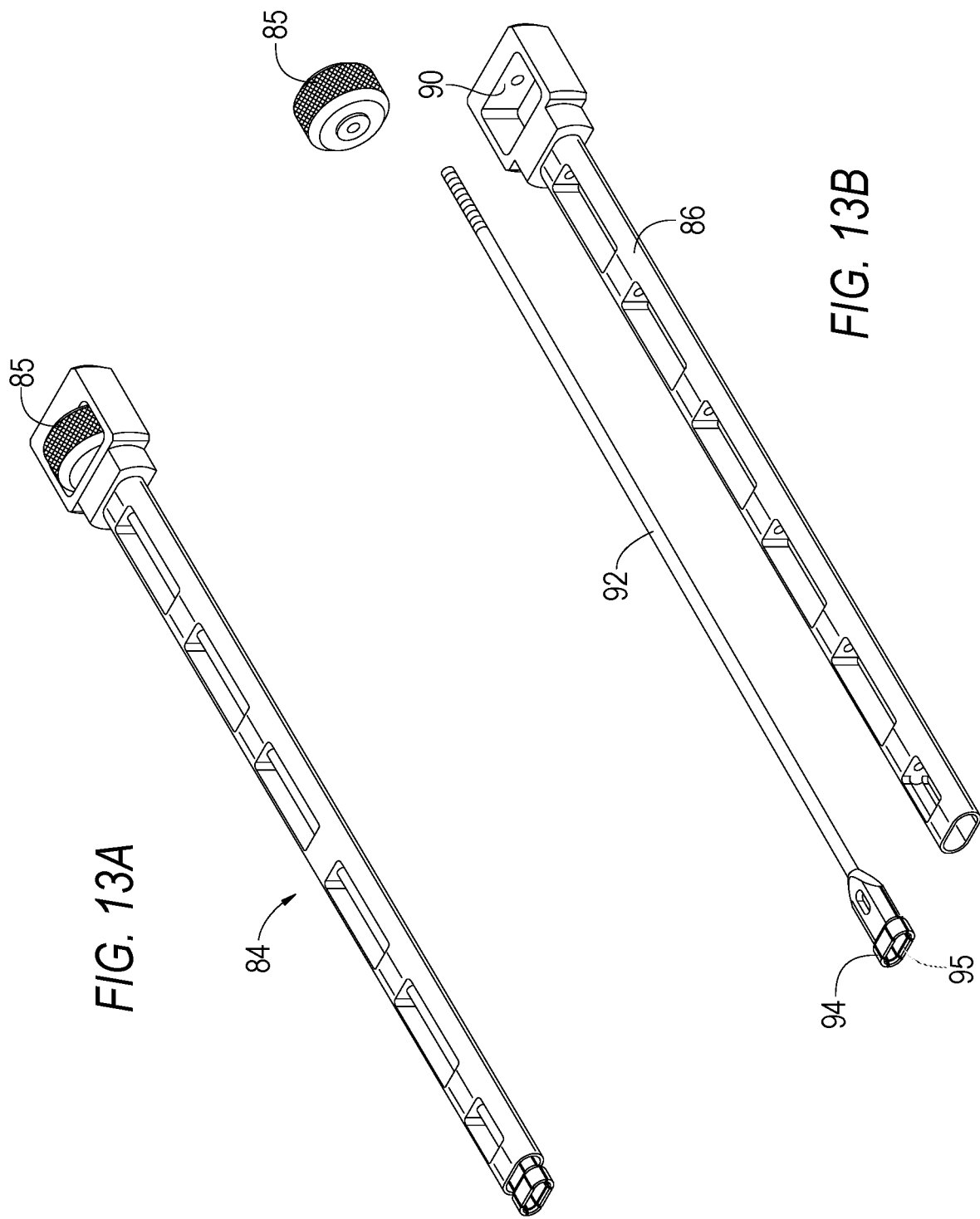

SURGICAL IMPLANT AND METHOD OF USING SAME

RELATED REFERENCES

This application is a continuation of and claims priority to U.S. application Ser. No. 15/722,603, filed on Oct. 2, 2017 and titled "Surgical Implant and Method of Using Same;" which claims priority to U.S. application Ser. No. 29/610,431, filed on Jul. 12, 2017, and titled, "Spinal Implant," the entire contents of which are incorporated herein by reference.

FIELD OF INVENTION

The present invention is directed to a surgical implant and, more particularly, a facet fusion implant and method of using same for fusing or stabilizing a facet joint.

BACKGROUND OF INVENTION

The facet joints are a set of synovial, plane joints between the articular processes of two adjacent vertebrae which help support the weight of the body and prevent excessive rotational motion of the spine. These joints are formed by bilateral protrusions of bone of one vertebra that intersect with respective bilateral protrusions of bone of the vertebra located above and the vertebra located below. In particular, superior processes projecting upward from a lower vertebra, their articular surfaces being directed more or less backward (oblique coronal plane), form facet joints with inferior processes projecting downward from a higher vertebra, their articular surfaces being directed more or less forward and outward.

Between each pair of facet joints lies a facet joint capsule composed of cartilage. If the cartilage wears away in the course of consistent motion, the facet joints can become a source of pain in areas ranging from the mid-back to upper-back, the neck to the base of the spine, and in the shoulders. This is referred to as facet joint arthritis or facet arthropathy.

A common and effective treatment for facet joint pain is facet joint fusion. This procedure involves removal of the joint cartilage or drilling a passageway through the joint and placement of a spacer into the joint or passageway in order to restrict the joint's movement and thereby cause bone fusion across the joint. Often, the spacer will take the form of a natural or synthetic bone dowel or bone graft that is inserted into the facet joint. The use of bone dowels presents advantages over metal implants such as screws which are typically inserted transversely through the intersecting facet joint bone protrusions. Advantages include a more efficacious bone fusion and permanent fixation once fusion is achieved.

Implantation of bone dowels between facet joints can be conducted using a minimally invasive procedure which takes place entirely through one or more cannulas inserted through a small incision in a patient's skin and muscle to provide direct access to the joint. Exemplary minimally invasive facet fusion procedures are described in U.S. Pat. Nos. 8,021,392 and 8,231,661. Alternatively, the procedure can be an open or mini-open procedure.

Although use of bone dowels for affecting facet joint fusion and stabilization often succeeds, in some instances dowels will migrate posteriorly out of the drilled passages before fusion can be achieved. This most often occurs if the walls of the passage formed through the joint capsule or joint are smooth or if the dowel fails to include anti-migration features such as fins or ribs. Additionally, undesired dowel migration can occur if the contact surface area between a dowel and the adjacent articular surfaces is too small to overcome the tendency of the dowel to back out of the joint. Accordingly, there is a need for a facet fusion implant configured for preventing undesired, posterior migration of the implant from facet joints.

BRIEF SUMMARY OF THE INVENTION

The present invention is directed to a facet fusion dowel and method of using same for fusing or stabilizing a facet joint. According to another aspect of the invention, there is provided a method of stabilizing a facet joint having a first articular surface and a second articular surface, the method including providing a fixation member with a stadium-shaped cross-section, forming a void having a substantially stadium-shaped cross-section within the facet joint and inserting the fixation member into the void. Utilization of a fixation member with a stadium-shaped cross-section maximizes the contact surface area between the fixation member and the articular surfaces of the facet joint. Stabilization is achieved by a precision press fit between the void and the fixation member, the fixation having a slight greater maximum circumference than the void. Thus, the pressure created by the opposing articular surfaces maintains the fixation member in place by an interference fit.

According to one embodiment of the present invention, the fixation member includes a tapered, anti-migration section configured for preventing the surgical implant from migrating posteriorly out of the facet joint by engaging the first articular surface and the second articular surface of the facet joint. The anti-migration section includes a variable width, a variable height, a stadium-shaped distal end, a stadium-shaped proximal end and a stepped sidewall including opposing first wall portions that define the variable width and opposing second wall portions that defined the variable height. The opposing first wall portions and the opposing second wall portions extend to and between the distal end and the proximal end. The fixation member can be constructed from biological materials such as bone and allograft bone or non-biological materials such as polyetheretherketone and titanium. The preferred material from which the fixation member is fabricated is cortical allograft bone derived from the femur or tibia.

According to another embodiment of the present invention, the void is formed by inserting a drill bit lengthwise between the first articular surface and the second articular surface to form a first passageway within the face joint, and inserting the drill bit lengthwise between the first articular surface and the second articular surface to form a second passageway within the facet joint. After forming the first and second passageways, the void has a cross-section appearing as two slightly overlapping circles. The drill bit is then inserted lengthwise between the first articular surface and the second articular surface a third time to form a third passageway within the face joint, the third passageway being located between the first passageway and the second passageway. After forming of the third passageway, the void exhibits the stadium-shaped cross-section. It is understood that the passageways can be formed using a single drill bit or multiple drill bits having different diameters. For example, the first and second passageways may be formed using a first drill bit and the third passageway may be formed using a second drill bit having a smaller or a larger diameter than the first drill bit.

According to another embodiment of the present invention, the void is formed by engaging a first drill guide with the facet joint, the first drill guide having two drill guide paths including a first path and a second path, and inserting a drill bit through the first path and lengthwise between the first articular surface and the second articular surface to form a first passageway within the face joint. The drill bit is then inserted through the second path and lengthwise between the first articular surface and the second articular surface to form a second passageway within the facet joint. Because the first and second paths extend parallel to one another and may overlap or be entirely separated, the first and second passageways extend parallel to one another and may overlap or be separate. After drilling of the two passageways, a second drill guide is engaged with the facet joint, the second drill guide including a unitary drill guide path. A drill bit is inserted through the unitary drill guide path and lengthwise between the first articular surface and the second articular surface to form a third passageway. The drill bit inserted into the second drill guide may be the same drill bit inserted through the first drill guide, or it may a different drill with a different radius.

According to another embodiment of the invention, there is provided a sterile surgical kit including a cannulated facet finder, a facet broach, a guide shaft, a dual drill guide, a first drill bit, a center drill guide, a second drill bit, an inserter and a fixation member with a stadium-shaped cross-section. The components of the kits may be hermetically sealed in a sterile metal or plastic tray or pouch.

According to yet another embodiment of the invention, the method of stabilizing a facet joint described herein may be used to provide fixation and additional columns of support as an adjunct to another fusion technique, e.g., posterolateral fusion or spinous process plating. Additionally, the method may be used posteriorly to complete an anterior/posterior fusion or a revision to supplement segment stability after a hardware removal or hardware failure.

BRIEF DESCRIPTION OF DRAWINGS

The disclosure can be better understood with reference to the following drawings. The elements of the drawings are not necessarily to scale relative to each other, emphasis instead being placed upon clearly illustrating the principles of the disclosure. Further, like reference numerals designate corresponding parts throughout the several views.

FIG. 7A is a perspective view of a cannulated facet finder in accordance with the present invention.

FIG. 7B is an exploded perspective view of the cannulated facet finder of FIG. 7A.

FIG. 8A is a perspective view of a facet broach in accordance with the present invention.

FIG. 8B is an exploded perspective view of the facet broach of FIG. 8A.

FIG. 9A is a perspective view of a guide shaft in accordance with the present invention.

FIG. 9B is an exploded perspective view of the guide shaft of FIG. 9A.

FIG. 10A is a perspective view of a dual drill guide in accordance with the present invention.

FIG. 10B is a magnified view of a proximal end of the dual drill guide of FIG. 10A.

FIG. 10C is a sectional view of the dual drill guide of FIG. 10A.

FIG. 11 is an elevational view of a first drill bit in accordance with the present invention.

FIG. 13A is a perspective view of an inserter in accordance with the present invention.

FIG. 13B is an exploded perspective view of the inserter of FIG. 13A.

DETAILED DESCRIPTION OF THE INVENTION

Figure 1:
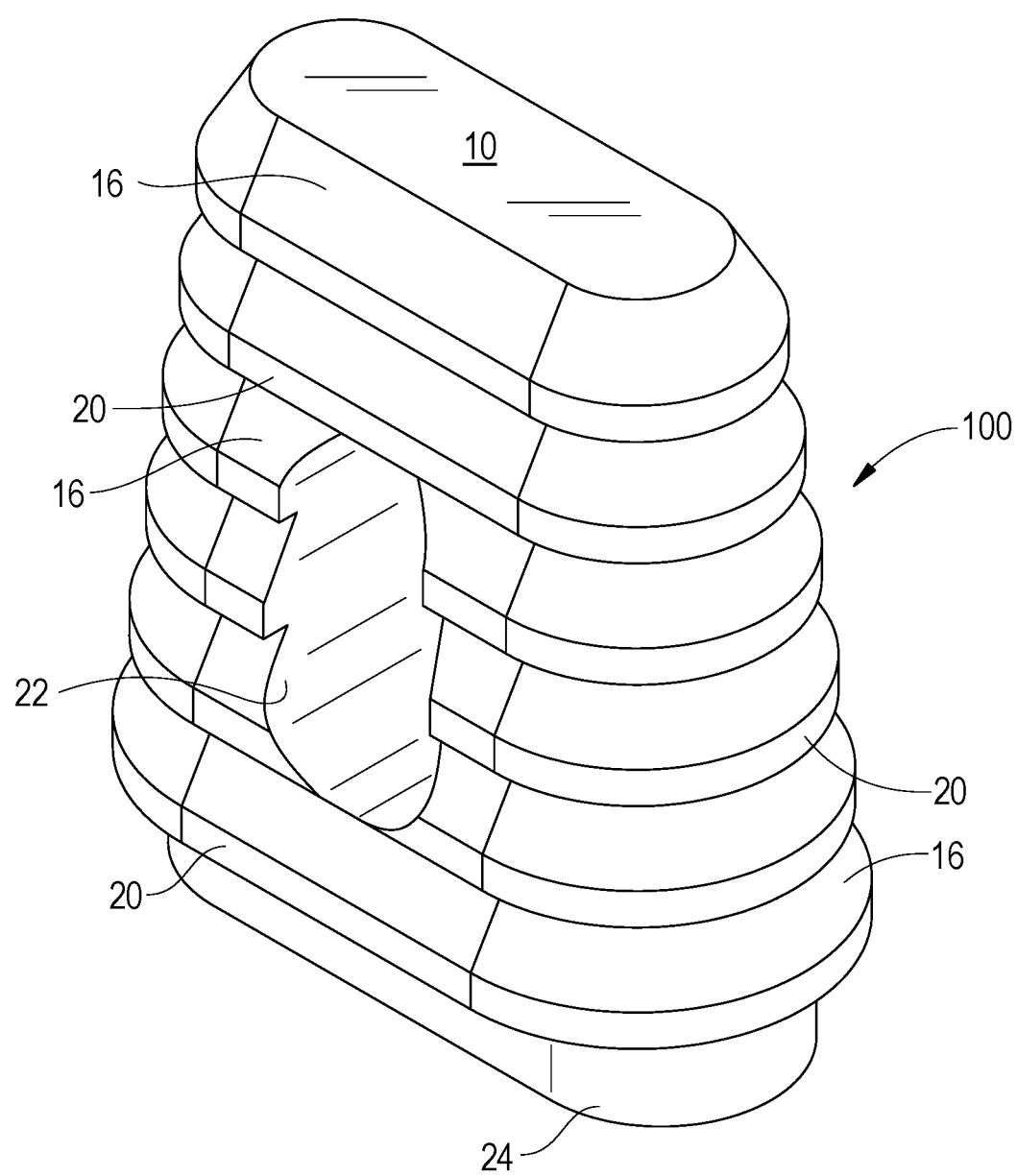
FIG. 1 is a perspective view of a surgical implant in accordance with the present invention.
Figure 2:
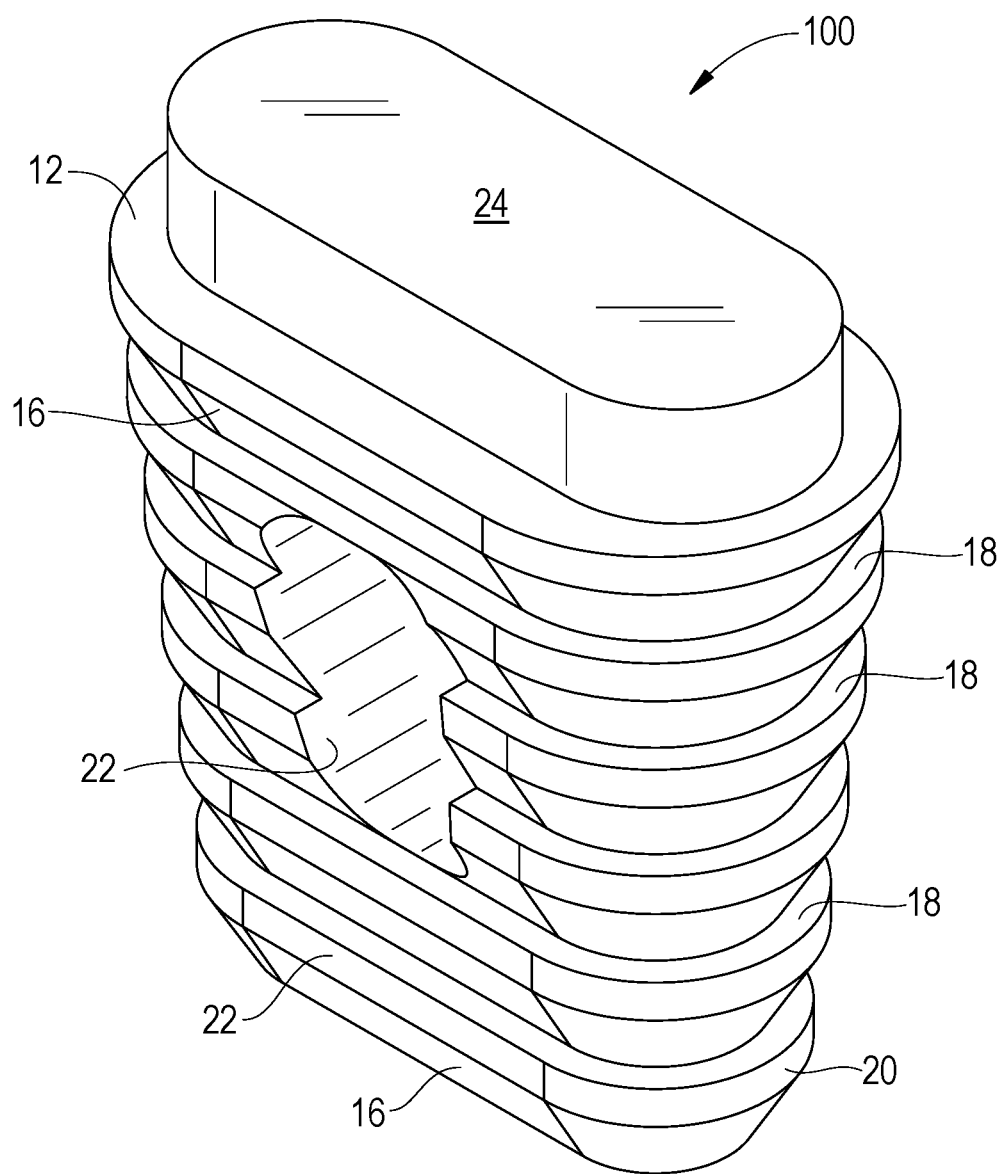
FIG. 2 is another perspective view of the surgical implant of FIG. 1
Figure 3:
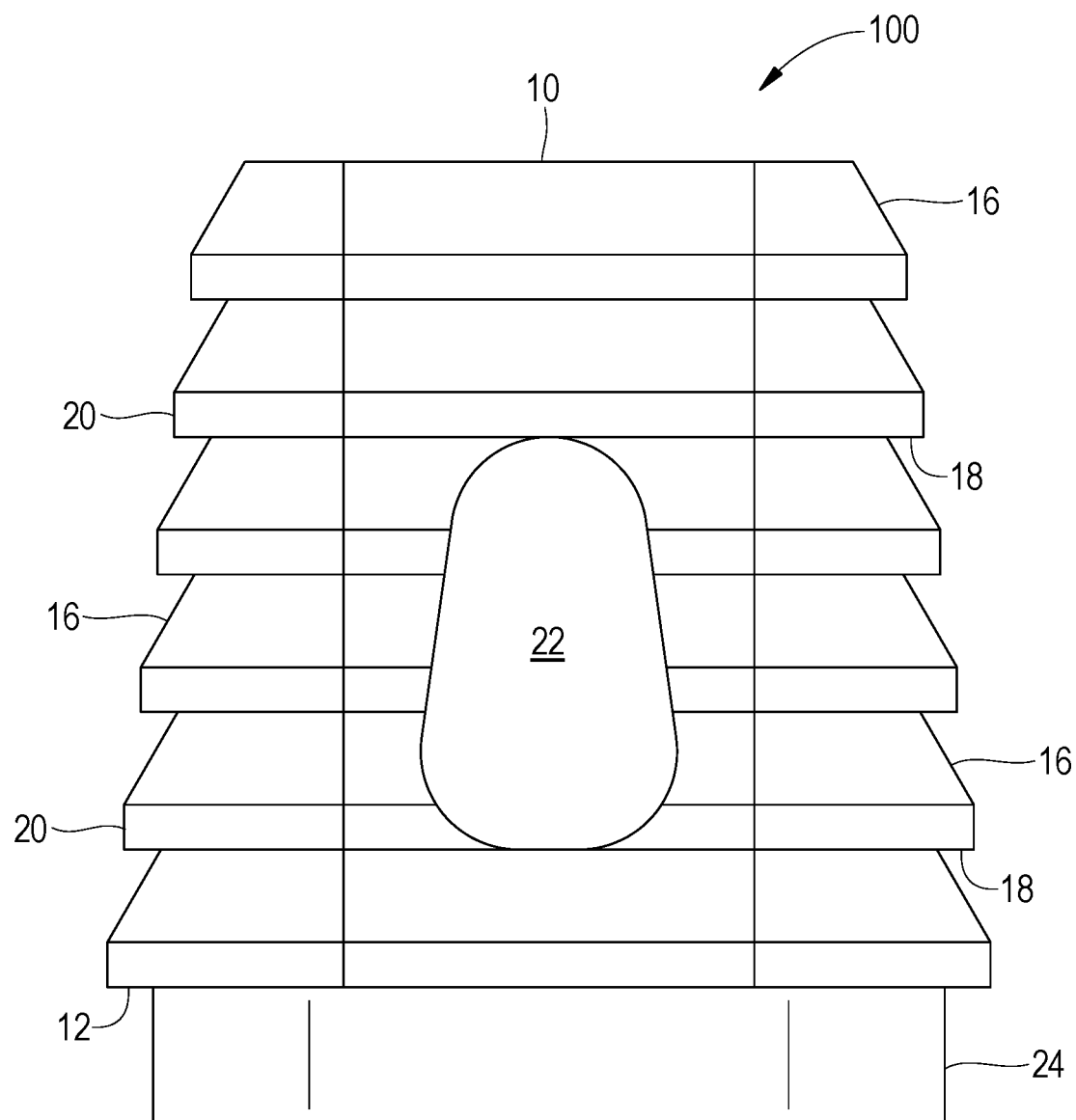
FIG. 3 is a plan view of the surgical implant of FIG. 1.
Figure 4:
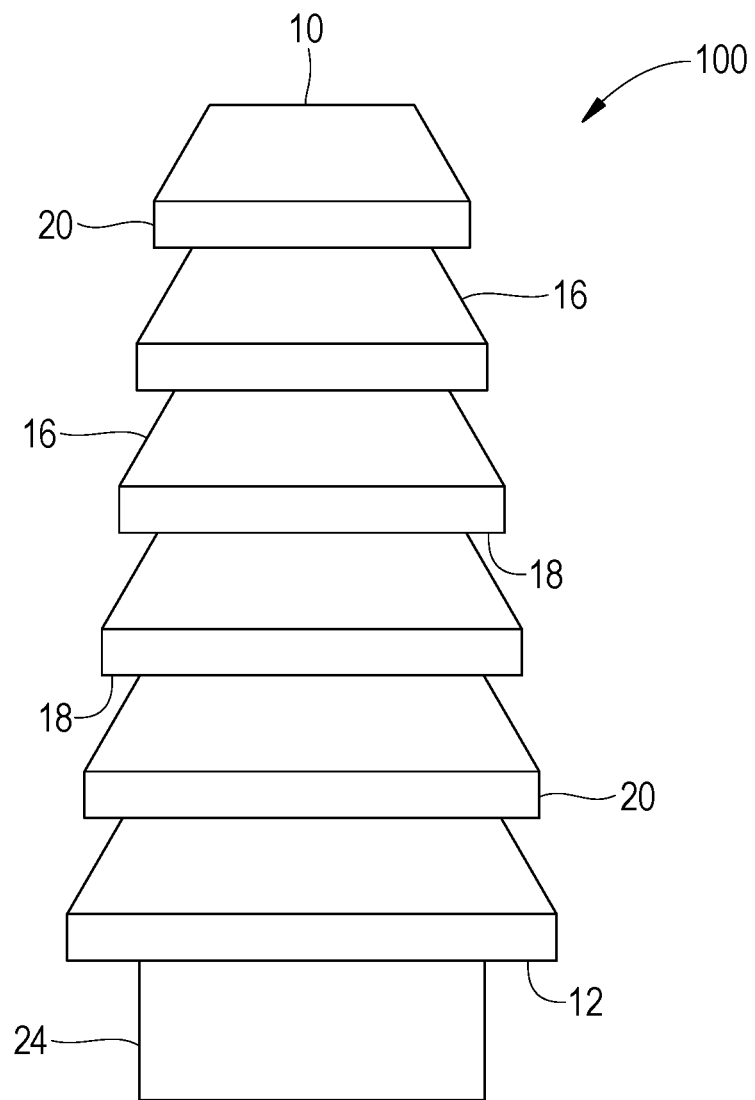
FIG. 4 is an elevational view of a lateral side of surgical implant of FIG. 1.
Figure 5:
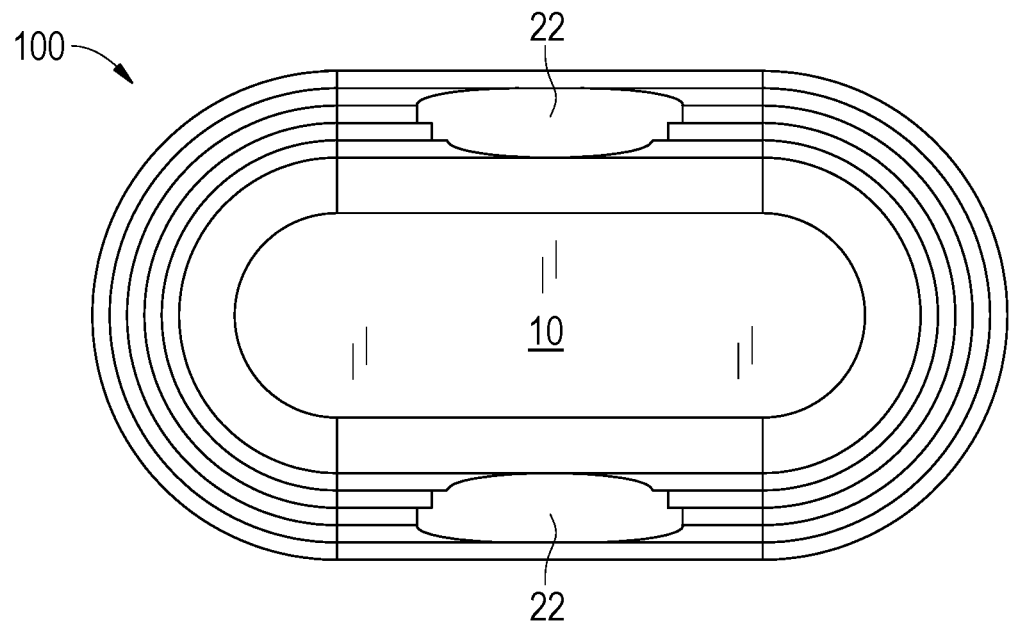
FIG. 5 is an elevational view of a distal end of the surgical implant of FIG. 1.
Figure 6:
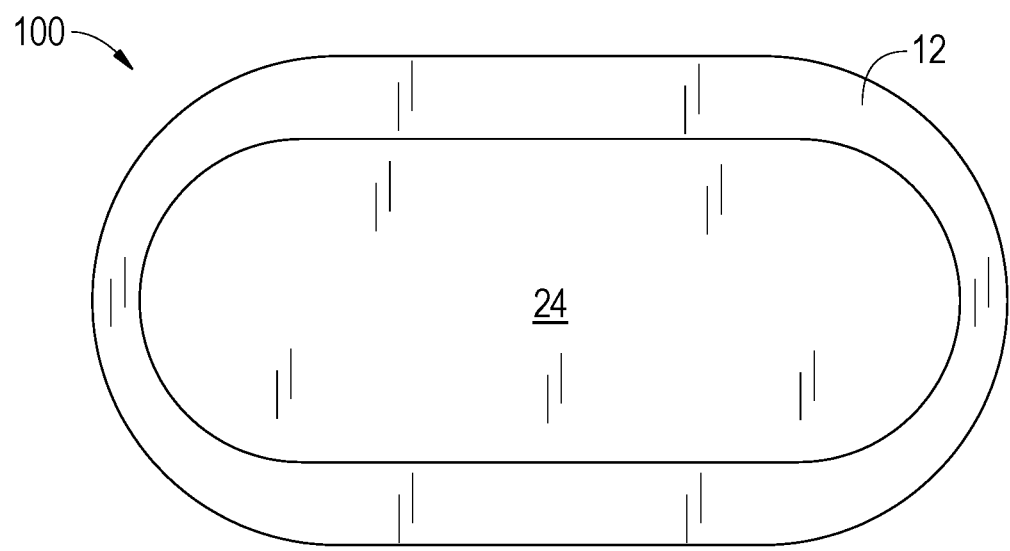
FIG. 6 is an elevational view of a proximal end of the surgical implant of FIG. 1.
Figure 12B:
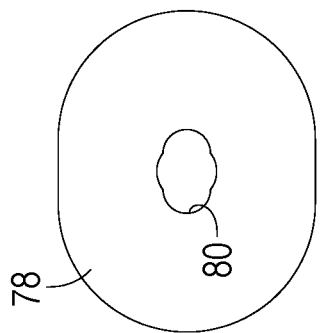
FIG. 12B is an elevational view of a proximal end of the center drill guide of the center drill guide of FIG. 12A.
Figure 12C:
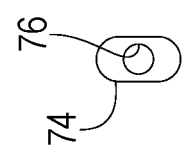
FIG. 12C is a sectional view of the center drill guide of FIG. 12A.
Figure 12A:
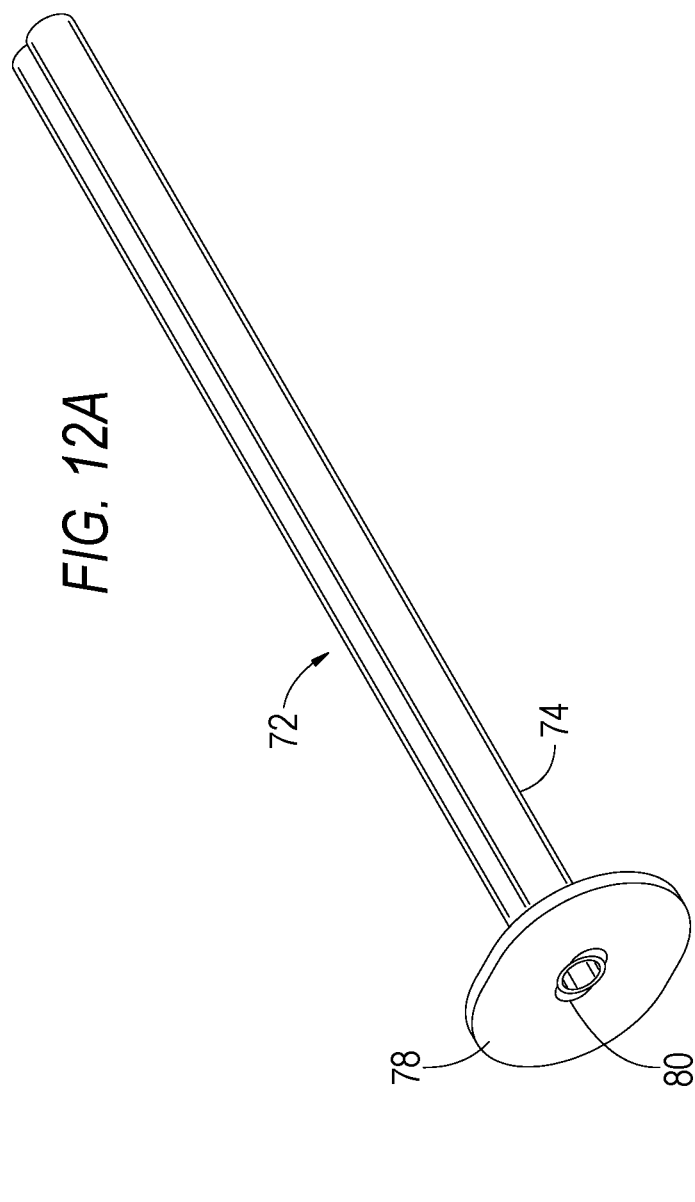
FIG. 12A is a perspective view of a center drill guide in accordance with the present invention.
Figure 12D:
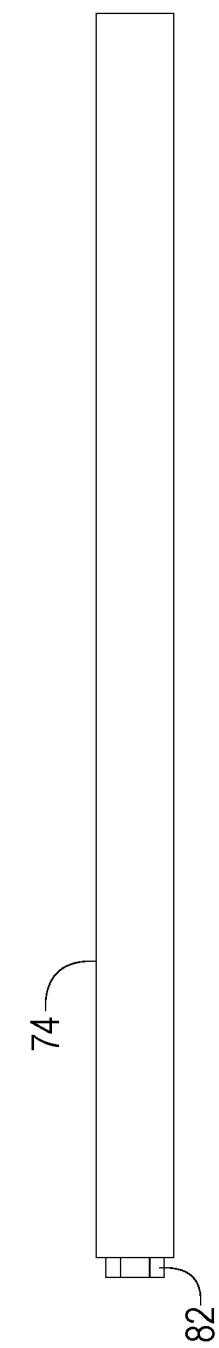
FIG. 12D is a plan view of the center drill guide of FIG. 21A.
Figure 14:
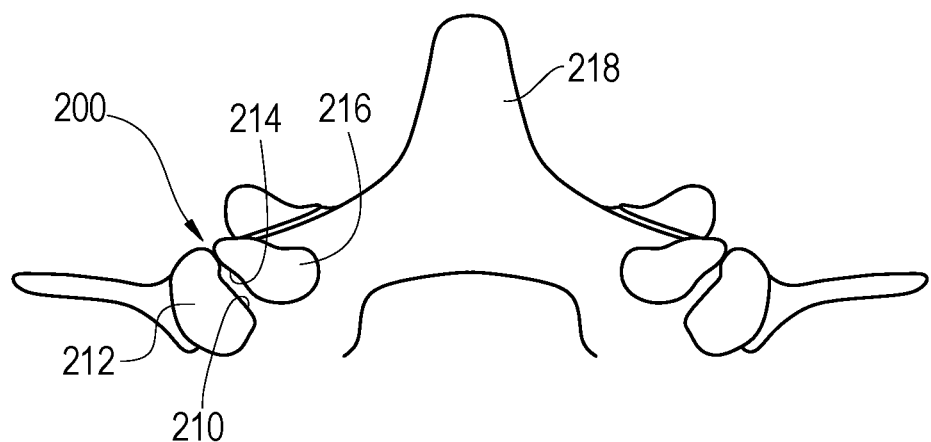
FIG. 14 is a sectional view of a facet joint.
Figure 15:
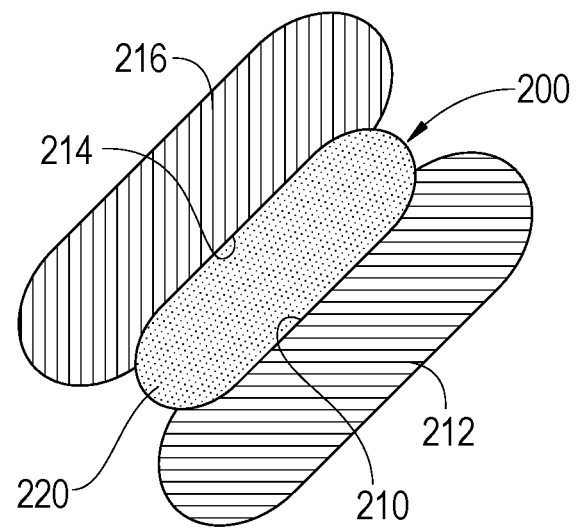
FIG. 15 is a plan view of a facet joint illustrating a void formed between articular surfaces of the joint in accordance with the present invention.
Figure 16:
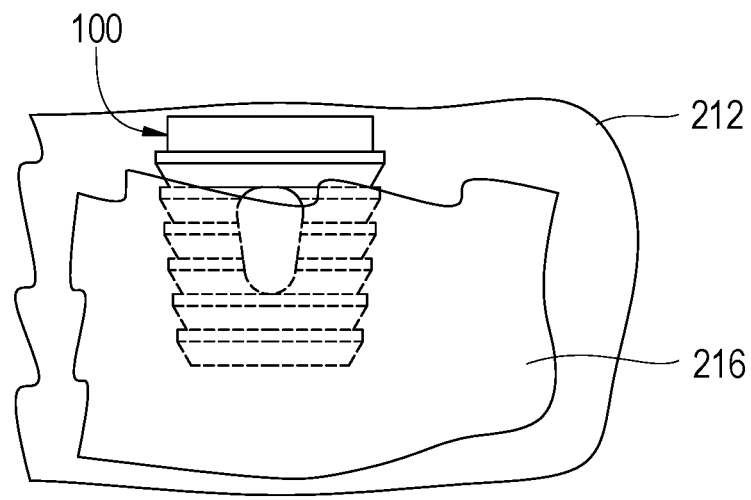
FIG. 16 is a partial sectional view of the surgical implant of FIG. 1 located within the void of FIG. 15.

The figures depict a facet fusion implant and method of inserting same into a facet joint in accordance with the present invention. In particular, FIGS. 1 through 6 depict a spinal implant 100, and FIGS. 7 through 13B depict surgical instruments used for locating a facet joint, preparing the facet joint for receiving implant 100 and inserting the implant between the articular surfaces of the facet joint. FIG. 14 depicts a facet joint, and FIGS. 15 and 16 depict a facet joint that has been for prepared for receiving and that has received implant 100.

Referring to FIGS. 1 through 6, implant 100 includes a tapered, anti-migration section configured for preventing the surgical implant from migrating posteriorly out of the facet joint by engaging a first articular surface and a second articular surface of a facet joint. The anti-migration section includes six stepped segments which extend between a stadium-shaped distal end 10 and a stadium-shaped proximal end 12 thereof. Stadium-shaped refers to a two-dimensional geometric shape constructed of a rectangle with semicircles at a pair of opposite sides. Each of the stepped segments includes a tapered wall portion 16 that tapers inwardly towards distal end 10 at an angle of about 60°, a vertical wall portion 18 that extends radially outward at a 900 angle from a longitudinal axis of implant 100 and a horizontal wall portion 20 that extends to and between tapered wall portion 16 and vertical wall portion 18 and intersects the vertical wall portion at a 900 angle. Horizontal wall portion 20 of each segment defines the greatest width and height of each segment, with the distance between the opposing rectangular or flat sides of the segment defining the height of the segment and the distance between the opposing semicircular sides defining the width of the segment. As best illustrated FIGS. 3-5, the heights and widths of the segments progressively decrease from the proximal-most segment to the distal-most segment. In particular, distal end 10 has a height of about 1.85 mm, the distal-most segment has a height of about 3 mm, the proximal-most segment and proximal side 12 each have a height of about 5 mm and a width of about 10 mm.

A hole 22 extends completely through the height of the anti-migration section and through the middle of three of the segments. Hole 22 has a length of about 4.5 mm as defined between its proximal and distal edges and provides a pathway through which bony fusion between the articular surfaces of the facet joint can occur.

Extending proximally from proximal side 12 is a centrally located protrusion 24 having a stadium-shaped cross-section. Protrusion 24 is configured for being received within an end of a device for grasping implant 100 and placing the implant within a facet joint. Combined, the anti-migration section and protrusion 24 have a length of about 10.50 mm.

Referring to FIGS. 7 through 13B, there are depicted surgical instruments in accordance with the present invention. In particular, FIGS. 7A and 7B depict a cannulated facet finder 26. Facet finder 26 includes a hollow, radiolucent finder shaft 28, a cannulated finder cap 30 disposed on a proximal end of the shaft and a radiopaque cannulated finder tip 32 disposed in a distal end of the shaft. Connecting pins 34 secure cap 30 and tip 32 to shaft 28. Surrounding the distal end of shaft 21 is a radiopaque band. This circular band allows the surgeon to easily target the point of the facet finder 26 using c-arm, fluoroscope, and/or x-ray technology in the operating room and make certain that the radiopaque tip 32 of the facet finder 26 is located in the center of the circle of the radiopaque band. Facet finder 26 may eliminate the need for a distraction tool.

FIGS. 8A and 8B depict a facet broach 36. Facet broach 36 is used in instances where the surgeon desires a degree of distraction of the facet joint 36 than cannot be accomplished with facet finder 26. Facet broach 36 includes a broach shaft 38, a broach cap 40, a broach tip 42 and connecting pins 44 for connecting cap 40 and tip 42 to shaft 38. When used, broach tip 42 is pushed into the facet joint a desired distance for producing the desired amount of joint distraction.

FIGS. 9A and 9B depict a guide shaft 46. Guide shaft 46 includes a radiolucent, hollow shaft 48 having a stadium-shaped cross-section that defines a stadium-shaped path 49 there through. Guide shaft 46 has a distal end terminating in a pair of teeth 50 and a proximal end opposite thereto configured for receiving a guide handle 52. Pins 51 attach guide handle 52 with shaft 48. Guide handle 52 includes a stadium-shaped opening 54 that is aligned with stadium-shaped path 49. For percutaneous surgery, pair of teeth 50 are used to lightly engage the guide shaft 46 into the facets, once the midline has been determined using facet finder 26 and fluoroscopy. For open surgery, the distal end of guide shaft 46 preferably has at least two teeth that are more aggressive (length and sharpness). Guide shaft 46 is tapped into place once the surgeon has visualized the correct placement location for implant 100.

FIGS. 10A, 10B and 10C, depict a dual drill guide 56. Dual drill guide 56 is provided to guide a drill bit in the formation of two, parallel passageways lengthwise through a facet joint. The cross-section of the passageways appears as two slightly overlapping circles. Dual drill guide 56 includes a dual drill guide shaft 58 defining a first path 60 and a second path 62 and a drill guide stopper 64 disposed on a proximal end of shaft 58 and having an opening 66 corresponding to first and second paths 60, 62.

FIG. 11 depicts a drill bit 68 with a shoulder stop 70. Drill bit 68 is provided for drilling a socket of desired depth into a spinal facet joint.

FIGS. 12A, 12B, 12C and 12D depict a center drill guide 72. Center drill guide 72 is provided to guide a drill bit in the formation of a single passageway lengthwise through a facet joint. The single passageway extends between the passageways formed using the dual drill guide. The cross-section of the resulting passageway is stadium-shaped. Center drill guide 72 includes a center drill guide shaft 74 defining a single path 76 there through. Disposed on a proximal end of shaft 74 is a center drill guide stopper 78 having an opening 80 comprised of a central, circular portion that corresponds to single path 76 and opposing lateral, rounded portions configured for receiving a proximal rim 82 of shaft 74 for securing the shaft to the stopper.

FIGS. 13A and 13B depict an implant inserter 84. Inserter 84 is provided to grasp implant 100 and insert the implant into the socket of the facets. Inserter 84 includes a shaft assembly 86, an inserter knob 85 rotatably supported within a proximal slot 90 of the assembly, an inserter collet rod 92 extending within the shaft assembly and operatively coupled to the knob and a flexible, collet member 94 coupled to a distal end of rod 92. Collet member 94 includes a female insertion interface 95 configured for receiving protrusion 24 of implant 100. Implant 100 is secured within interface 95 by inserting protrusion 24 into interface 95 and rotating knob 85, which retracts collect member 94 within a distal end of shaft assembly 86. As collet member 94 enters into the distal end of assembly 86, female insertion interface 95 is compressed by the walls of the distal end of assembly 86, causing the interface to press upon protrusion 24. Once engaged, inserter 84 holds implant 100 such that the entire circumference of the anti-migration portion of implant 100 is visible to the surgeon. Implant is disengaged from inserter 84 by rotating knob 85 in the reverse direction which moves collet member 94 out of the distal end of shaft assembly 86 thereby decompressing collet member 94. As a consequence, implant 100 is loosely held by inserter 84 and thus easily removed therefrom.

It is contemplated that implant 100 and the instruments depicted in FIGS. 7 through 13B may be sterilely packaged within a pouch or tray to form a surgical kit for a facet fusion surgical procedure. The kit may include two implants 100 when a bilateral facet fusion is intended. Further, it may include additional instruments such as expansion cannulas when the procedure is a minimally invasive procedure, scalpels, scissors and retractors.

Referring to FIG. 14, there is depicted a facet joint 200. Facet joint 200 is formed between an articular surface 210 of a superior process 212 of a lower vertebra and an articular surface 214 of an inferior process 216 of a higher vertebra 218. Located between articular surfaces 210 and 214 lies a facet joint capsule composed of cartilage. There are two methods for positioning the allograft implant 100 into the socket drilled into the facets. One is a percutaneous or minimally-invasive method, and the other is an open method.

In the minimally invasive method the graft site is prepared according to standard procedures. A wire is inserted through a small incision in the patient's skin and into the joint thereby providing an approach to the joint. Facet finder 26 is then placed over the wire and lowered so that the wire passes through cannulated finder tip 23, finder shaft 28 and cannulated finder cap 30. Approximation of the midline of the facet joint is made using fluoroscopy and the wire is removed. Thereafter, guide shaft 46 is slid over facet finder 26 such that the guide shaft 46 encircles the intended surgical site. Light tapping on top of guide shaft 46 with a mallet sets teeth 50 of guide shaft 46 within the joint. Facet finder 26 is removed through the top of the guide shaft 46 leaving guide shaft 46 in place and engaged with the joint.

If increased distraction of the joint is required at any time during the facet fusion procedure, facet broach 36 may be inserted through guide shaft 46 and into the facet joint. The greater the desired the distraction, the farther broach tip 42 is inserted into the joint. Broach tip 42 is advanced into the joint by tapping broach cap 40 with a mallet.

After guide shaft 46 is in place within the joint, dual drill guide 56 is inserted through the top of guide shaft 46 to provide two pathways through which drill bit 68 is passed for forming two passageways through the facet joint. The passageways define respective axes that extend parallel to one another and lengthwise through the joint. The passageways may be spaced apart or slightly overlapping. Drilling into the joint causes the cutting away of cartilage of the joint capsule and bone of the opposing facet joint processes. The facet joint is drilled to a desired depth by arresting distal movement of drill bit 68 by bearing shoulder stop 70 of the drill bit on guide stopper 64 of dual drill guide 56. Drill bit 68 is removed leaving the guide shaft 46 in place.

Center drill guide 72 is then inserted through the top of guide shaft 46 to provide a single pathway through which drill bit 68 is passed for forming a single passageway through the facet joint and facet joint capsule. The single pathway defines an axis that extends between the axes of the two passageways formed using dual drill guide 56. Referring to FIG. 15, the resulting void 220 exhibits a stadium-shaped cross-section that extends lengthwise into the joint and between the joint and through the joint capsule. Drill bit 68 is removed leaving the guide shaft 46 in place.

Implant 100 is then placed into inserter 84. The inserter 84, holding implant 100, is placed through guide shaft 46 and loaded into the prepared socket. The surgeon rotates knob 85 thereby releasing until implant 100 within the prepared socket. Inserter 84 is then removed, leaving implant 100 properly placed, as shown FIG. 16. Guide shaft 46 is removed. Typically, the procedure is repeated with the contralateral facet joint. The patient is closed according to standard procedures.

In the open method the graft site is prepared according to standard procedures. Guide shaft 46 is inserted along the plane of the facet joint. Guide shaft 46 is firmly seated in place, with pair of teeth 50 engaged in the facet joint. Dual drill guide 56 is then inserted through the top of guide shaft 46 to provide two pathways through which drill bit 68 is passed for forming two passageways through the facet joint. Drill bit 68 is removed, leaving the guide shaft 46 in place. Center drill guide 72 is then inserted through the top of guide shaft 46 to provide a single pathway through which drill bit 68 is passed for forming a single passageway through the facet joint and facet joint capsule. The single pathway extends between the two passageways formed using dual drill guide 56. The resulting void 220 exhibits a stadium-shaped cross-section that extends lengthwise between the joint and through the joint capsule. Drill bit 68 is removed, leaving the guide shaft 46 in place. Implant 100 is then placed into inserter 84, placed through guide shaft 46 and loaded into the prepared socket. Inserter 84 is removed, leaving implant 100 properly placed, as shown FIG. 16. Guide shaft 46 is removed. Typically, the procedure is repeated with the contralateral facet joint. The patient is closed according to standard procedures.

Facet fusion using the methods of the present invention is minimally invasive, even using the open procedure, because less tissue is destroyed in this process than in typical spinal fusion. In many cases, facet fusion by the presents methods provides pain relief obviating the need for traditional spinal fusion and use of traditional metal hardware. Alternatively, the facet fusion method can be used as an adjunct to traditional spinal surgery and the use of traditional spinal hardware.

The facet fusion methods of the present invention can stabilize any given spinal segment to reduce painful motion and to accomplish fusion. This spinal stabilization method allows for accelerated rehabilitation, shorter hospital stays, shorter surgical procedures, and reduces muscle, ligament and soft tissue trauma. Since the facet fusion methods of the present invention are preformed bilaterally, they provide for posterior fusion with two columns of support within the spine. The procedures provide immediate pain relief in many, if not most, cases and are quickly learned by surgeons who do spinal surgeries.

As will be apparent to one skilled in the art, various modifications can be made within the scope of the aforesaid description. Such modifications being within the ability of one skilled in the art form a part of the present invention and are embraced by the claims below.

What is claimed is:

1. A surgical implant for stabilizing a facet joint having a first articular surface and a second articular surface comprising:
   a stadium-shaped cross-section,
   a distal end,
   a stadium-shaped proximal end including a smooth convex proximal end sidewall and a flat proximal end terminus, the stadium-shaped proximal end configured for being received within an end of a device for grasping the surgical implant by compressive force and placing the surgical implant within the facet joint,
   a height,
   a longitudinal axis extending through the proximal end and the distal end,
   a plurality of segments, each segment of the plurality of segments including a tapered wall portion that tapers inwardly towards the distal end, a vertical wall portion that extends radially outward from the longitudinal axis and a horizontal wall portion that extends to and between the tapered wall portion and vertical wall portion, and
   a hole extending completely through the height of the implant, through the longitudinal axis and through at least two segments of the plurality of segments, the hole being configured for providing a pathway through which bony fusion between the first articular surface and the second articular surface can occur.

2. The surgical implant of claim 1 including a tapered, anti-migration section configured for preventing the surgical implant from migrating posteriorly out of the facet joint by engaging the first articular surface and the second articular surface of the facet joint, the anti-migration section including a variable width, a variable height, and a stepped sidewall including opposing first wall portions that define the variable width and opposing second wall portions that define the variable height, the opposing first wall portions and the opposing second wall portions extending to and between the distal end and the proximal end.

3. The surgical implant of claim 1 including an anti-migration section that extends to and between the distal end and the proximal end, a length and a width of the proximal end of the anti-migration section being the same.

4. The surgical implant of claim 3 wherein the proximal end of the anti-migration section has a height that is half of the width thereof.

5. The surgical implant of claim 1 including a tapered, anti-migration section having a stadium-shaped cross-section.

6. The surgical implant of claim 1 wherein, for at least one segment of the plurality of segments, the tapered wall portion tapers inwardly towards the distal end at an angle of 60°, the vertical wall portion extends radially outward at a 90° angle from the longitudinal axis and the horizontal wall portion intersects the vertical wall portion at a 90° angle.

7. A surgical implant for stabilizing a facet joint having a first articular surface and a second articular surface comprising:
   a tapered, anti-migration section configured for preventing the surgical implant from migrating posteriorly out of the facet joint by engaging the first articular surface and the second articular surface of the facet joint, the anti-migration section having a stadium-shaped distal end, a stadium-shaped proximal end including a smooth convex proximal end sidewall and a flat proximal end terminus, the stadium-shaped proximal end configured for being received within an end of a device for grasping the surgical implant by compressive force and placing the surgical implant within the facet joint, and a stepped sidewall extending to and between the distal end and the proximal end, wherein the stepped sidewall defines a height of the surgical implant and includes at least one segment having a tapered wall portion that tapers inwardly towards the distal end, a vertical wall portion that extends radially outward from a longitudinal axis of the implant and a horizontal wall portion that extends between the tapered wall portion and the vertical wall portion, and
   a hole extending completely through the height of the implant, through the longitudinal axis and through the least one segment, the hole being configured for providing a pathway through which bony fusion between the first articular surface and the second articular surface can occur.

8. The surgical implant of claim 7 wherein the tapered wall portion tapers inwardly towards the distal end at an angle of 60°, the vertical wall portion extends radially outward at a 90° angle from the longitudinal axis and the horizontal wall portion intersects the vertical wall portion at a 90° angle.

9. A surgical implant for stabilizing a facet joint having a first articular surface and a second articular surface comprising:
   a stadium-shaped proximal end including a smooth convex proximal end sidewall and a flat proximal end terminus, the stadium-shaped proximal end configured for being received within an end of a device for grasping the surgical implant by compressive force and placing the surgical implant within the facet joint,
   a step defining a height of the implant, the step including a tapered wall portion, a vertical wall portion and a horizontal wall portion that extends to and between the tapered wall portion and vertical wall portion, and
   a hole extending completely through the height of the implant, the tapered wall portion, the vertical wall portion and the horizontal wall portion, the hole being configured for providing a pathway through which bony fusion between the first articular surface and the second articular surface can occur.

10. The surgical implant of claim 9, wherein the tapered wall portion tapers inwardly at an angle of 60°, the vertical wall portion extends radially outward at a 90° angle from a longitudinal axis of the implant and the horizontal wall portion intersects the vertical wall portion at a 90° angle.

* * * * *